(12) United States Patent
Mennen

(10) Patent No.: US 6,680,407 B2
(45) Date of Patent: Jan. 20, 2004

(54) INSTALLATION AND PROCESS FOR THE PREPARATION OF UREA

(75) Inventor: Johannes Henricus Mennen, Roggel (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/239,744

(22) PCT Filed: Jan. 29, 2001

(86) PCT No.: PCT/NL01/00062

§ 371 (c)(1),
(2), (4) Date: Sep. 26, 2002

(87) PCT Pub. No.: WO01/72700

PCT Pub. Date: Oct. 4, 2001

(65) Prior Publication Data

US 2003/0088126 A1 May 8, 2003

(30) Foreign Application Priority Data

Mar. 27, 2000 (NL) .............................................. 1014756

(51) Int. Cl.⁷ .............................................. C07C 273/04
(52) U.S. Cl. .............................. 564/72; 564/66; 564/67; 564/69; 564/70; 564/71; 422/149; 422/187; 422/189; 422/196; 422/197; 422/202; 422/203; 422/204

(58) Field of Search .............................. 564/66, 67, 69, 564/70, 71, 72; 422/149, 187, 189, 196, 197, 202, 203, 204

(56) References Cited

U.S. PATENT DOCUMENTS 3,406,201 A    10/1968   Baumann et al. ........... 260/555
6,476,262 B2 *  11/2002   Fukunaka et al. ............ 564/67

* cited by examiner

Primary Examiner—Peter O'Sullivan
(74) Attorney, Agent, or Firm—Pillsbury Winthrop LLP

(57) ABSTRACT

The invention relates to an installation for the preparation of urea from ammonia and carbon dioxide, the installation comprising two reactor sections in a vertically placed combined reactor and a high-pressure condenser section. The installation may comprise a vertically placed combined reactor, with the two reactor sections being separated by a high-pressure condenser section. In another embodiment the installation comprises a vertically placed combined reactor that comprises two reactor sections and a high-pressure condenser section placed outside the reactor. The invention also relates to a process for the preparation of urea in this installation. This involves feeding the gas stream leaving the stripper wholly or partly to the high-pressure condenser section of the installation. Preferably, a portion of the gas stream leaving the scrubber is fed to the second reactor section in the vertically placed combined reactor via an ammonia-driven ejector.

21 Claims, 7 Drawing Sheets

INSTALLATION AND PROCESS FOR THE PREPARATION OF UREA

CROSS REFERENCE TO RELATED APPLICATION

This application is the National Phase of International Application PCT/NL01/00062 filed Jan. 29, 2001 which designated the U.S., the entirety of which is incoporated herein by reference.

The invention relates to an installation for the preparation of urea. The invention also relates to a process for the preparation of urea in this installation.

Urea can be prepared by introducing an ammonia excess together with carbon dioxide at a pressure between 12 and 40 MPa and at a temperature between 150 and 250° C. into a urea synthesis zone. The resulting urea formation can be represented best in the form of two consecutive reaction steps, in the first step ammonium carbamate being formed according to the exothermic reaction:

$$2NH_3 + CO_2 \rightarrow H_2N\text{—}CO\text{—}ONH_4$$

after which the ammonium carbamate formed is dehydrated in the second step to give urea according to the endothermic equilibrium reaction:

$$H_2N\text{—}CO\text{—}ONH_4 \leftrightarrow H_2N\text{—}CO\text{—}NH_2 + H_2O$$

The extent to which these reactions take place depends amongst other things on the temperature and the ammonia excess used. The reaction product obtained is a urea synthesis solution substantially consisting of urea, water, unbound ammonia and ammonium carbamate. The ammonium carbamate and the ammonia are removed from the solution and are preferably returned to the urea synthesis zone. In addition to the above-mentioned solution in the urea synthesis zone a gas mixture is formed which consists of unconverted ammonia and carbon dioxide together with inert gases, the so-called reactor off-gas. Ammonia and carbon dioxide are removed from this gas mixture and are preferably also returned to the urea synthesis zone. The urea synthesis zone may comprise separate zones for the formation of ammonium carbamate and urea. These zones may, however, also be combined in a single apparatus.

In practice, various processes are used for the preparation of urea. At first, urea was prepared in so-called conventional high-pressure urea plants. At the end of the 1960s, however, this process was succeeded by processes carried out in so-called urea stripping plants.

The conventional high-pressure urea plants that are currently still operating are understood to be urea plants in which the decomposition of the ammonium carbamate not converted into urea and the expulsion of the usual ammonia excess take place at a substantially lower pressure than the pressure in the synthesis reactor itself. In a conventional high-pressure urea plant the synthesis reactor is usually operated at a temperature of 180–250° C. and a pressure of 15–40 MPa. Furthermore, in a conventional high-pressure urea plant ammonia and carbon dioxide are fed directly to the urea reactor. In a conventional high-pressure urea process the molar $NH_3/CO_2$ ratio (=N/C ratio) in the urea synthesis zone lies between 3 and 6. Depending on the extent to which the unconverted ammonia and carbon dioxide are returned to the urea synthesis section in conventional urea plants, a distinction is made between Once Through (no recycle), Partial Recycle (only partial recycle of ammonia and/or carbon dioxide) or Total Recycle (both ammonia and carbon dioxide recycle) plants.

A urea stripping plant is understood to be a urea plant in which the decomposition of the ammonium carbamate that has not been converted into urea and the expulsion of the usual ammonia excess largely take place at a pressure that is essentially almost equal to the pressure in the synthesis reactor. This decomposition and expulsion take place in one or more stripper(s) installed downstream of the synthesis reactor, preferably with the aid of a stripping gas such as, for example, carbon dioxide and/or ammonia, and with addition of heat. It is also possible to apply thermal stripping. Thermal stripping means that use is made exclusively of the supply of heat to decompose ammonium carbamate and remove the ammonia and carbon dioxide present from the urea synthesis solution. The gas stream containing ammonia and carbon dioxide that leaves the stripper is condensed in a high-pressure condenser and then returned to the urea synthesis zone.

The gas mixture that has not reacted in the urea synthesis zone of a urea stripping plant is removed from the urea synthesis zone and absorbed at synthesis pressure, for example in a high-pressure scrubber. In such a high-pressure scrubber the condensable components, ammonia and carbon dioxide, are preferably absorbed from the reactor off-gas into a low-pressure carbamate stream formed in the further recovery. The carbamate stream from the high-pressure scrubber, which contains the ammonia and carbon dioxide absorbed from the reactor off-gas, is returned to the urea synthesis zone, optionally via the high-pressure carbamate condenser. The reactor, high-pressure scrubber, stripper and high-pressure condenser are the most important elements of the high-pressure section of a urea stripping plant.

In a urea stripping plant the synthesis reactor is operated at a temperature of 160–240° C. and preferably at a temperature of 170–220° C. The pressure in the synthesis reactor is 12–21 MPa, preferably 12.5–19 MPa. The N/C ratio in the urea synthesis zone of a stripping plant lies between 2.5 and 5. The synthesis can be carried out in a single reactor or in a plurality of reactors arranged in parallel or in series. When use is made of two reactors in parallel, for example, the first reactor can be operated using virtually fresh raw materials and the second using raw materials entirely or partly recycled, for example from the urea recovery.

A frequently used embodiment for the preparation of urea according to a stripping process is the Stamicarbon $CO_2$ stripping process as for example described in European Chemical News, Urea Supplement, of Jan. 17, 1969, pages 17–20. The high-pressure condenser in a Stamicarbon $CO_2$ stripping process is preferably designed as a submerged high-pressure condenser a so called poolcondensor, as described in NL-A-8400839.

After the stripping treatment, the pressure of the stripped urea synthesis solution is reduced in the urea recovery and the solution is evaporated, after which urea is recovered. This produces a low-pressure carbamate stream in the recovery. This low-pressure carbamate stream is preferably returned via the high-pressure scrubber to the urea synthesis zone operating at synthesis pressure.

In a particular embodiment of a urea stripping process the functions of reactor and poolcondenser are combined in a single high-pressure vessel with the functionalities of these process steps being separated by partition walls designed for small pressure differences in this high-pressure vessel. An example of such an embodiment is described in Nitrogen No. 222, July–August 1996, pages 29–31, which describes the poolreactor, as does U.S. Pat. No. 5,767,313. This poolreactor is placed in a horizontal position.

The disadvantage of this horizontal position is that the horizontally placed poolreactor takes up a great deal of space and must also be placed at a greater height in order to enable the urea synthesis solution to be transferred to the stripper by gravity. This necessitates high investments.

The aim of the present invention now is to provide an installation comprising an improved reactor for the preparation of urea which requires lower investment costs. The aim of the present invention is also to provide an improved process for the preparation of urea in an installation comprising this reactor.

The applicant has found an improved installation for the preparation of urea from ammonia and carbon dioxide, which is characterized in that the installation comprises two reactor sections in a vertically placed combined reactor and a high-pressure condenser section.

In particular, the installation in a first embodiment comprises a vertically placed combined reactor comprising two reactor sections that are separated by a high-pressure condenser section. In a second embodiment the installation comprises a vertically placed combined reactor comprising two reactor sections and a high-pressure condenser section placed outside the combined reactor.

More in particular the applicant has found improved installations in which in the first embodiment the vertically placed combined reactor consists of a first reactor section in which a scrubber is present, a high-pressure condenser section and a second reactor section, with the high-pressure condenser section being located below the first reactor section in which the scrubber is placed and above the second reactor section. Preferably, the high-pressure condenser section in the combined reactor is designed as a submerged high-pressure condenser. In the second embodiment the vertically placed reactor comprises two reactor sections, with the second reactor section being located below the first reactor section, in which the scrubber is installed. The high-pressure condenser section is placed outside the combined reactor in the second embodiment of the installation. Preferably, this high-pressure condenser section placed outside the combined reactor is located below the scrubber of the first reactor section, so that the transfer of the carbamate from the scrubber to the high-pressure condenser takes place by gravity. Preferably, the carbamate is transferred from the scrubber to the high-pressure condenser through a downcomer. Preferably, the high-pressure condenser section placed outside the combined reactor is a horizontally placed high-pressure condenser and more in particular a submerged high-pressure condenser as described in EP-A-1 55 735.

The applicant has also found an improved process for the preparation of urea from ammonia and carbon dioxide, which is characterized in that the preparation takes place wholly or partly in an installation comprising two reactor sections in a vertically placed combined reactor and a high-pressure condenser section. In particular, the applicant has found an improved process for the preparation of urea from ammonia and carbon dioxide in which the preparation takes place wholly or partly in an installation in which the vertically placed reactor comprises two reactor sections that are separated by a high-pressure condenser section. In another embodiment the preparation of urea from ammonia and carbon dioxide takes place wholly or partly in an installation in which the vertically placed combined reactor comprises two reactor sections and in which the high-pressure condenser section is placed outside the combined reactor.

The process for the preparation of urea from ammonia and carbon dioxide is characterized in particular in that the gas stream leaving the stripper is fed to the high-pressure condenser section of the installation. More in particular this gas stream is wholly or partly condensed in the carbamate stream which is transferred from the scrubber section to the high-pressure condenser section through a downcomer.

The vertically placed combined reactors in the installation are generally designed as a wide pipe with a diameter between 1 and 5 metres, preferably between 2 and 4 m. The length of the combined reactor is in general between 5 and 70 metres, preferably between 10 and 40 metres.

The pressure conditions in the reactor, scrubber and high-pressure condenser sections of the installation are virtually equal and are such that the reactor sections and the high-pressure condenser section are operated at a high pressure. Preferably, the pressure lies between 12 and 22 MPa, in particular between 13 and 21 MPa. The temperature in the reactor sections and in the high-pressure condenser sections lies between 150 and 250° C., preferably between 170 and 200° C.

The reactor sections of the vertically placed combined reactor in the installation are in general provided with means that ensure that the synthesis solution preferably flows through the reactor sections as a plug flow. For this purpose the reactor sections are provided with for example a structured packing (in one or more locations) or they are divided, for example with the aid of sieve plates, into compartments of virtually equal volume, so that a cascade-type reactor is formed and therefore plug flow is approached. The sieve plates used can be of any type as described in the literature on urea production. The compartments form a succession of "continuously stirred tank reactors" (CSTRs), as it were.

The number of compartments in the reactor sections of the combined reactor, as series-arranged CSTRs, is preferably larger than 2 and in particular larger than 5. In general, the number of compartments, as CSTRs, will be smaller than 40 and preferably smaller than 20.

The compartments in the reactor sections of the combined reactor are preferably formed by virtually horizontally placed sieve plates. These preferably have a surface area that is at least 50% of the surface area of the horizontal cross-section of the vertically placed reactor and preferably at least 85%. In particular, the sieve plates have a surface area that is virtually equal to 100% of the horizontal cross-section of the vertically placed reactor.

The heat released in the high-pressure condenser section of the installation can be removed by means of water that is passed through or around the tubes of a heat exchanger, in which process it is converted into low-pressure steam of for example 0.3–1 MPa. The heat can be removed also by passing through a process stream that is to be heated, for example a urea solution to be evaporated. The heat exchanger is preferably installed in the high-pressure condenser section of the installation. If it is placed between the two reactor sections of the vertically placed combined reactor, this high-pressure condenser section takes up 10–70% of the total length of the combined reactor, and preferably 20–50%.

The stripping gases can be distributed in the installation for example by means of a distribution bubble cap in the bottom of the high-pressure condenser and they can be wholly or partially condensed in the carbamate stream coming from the scrubber section through a downcomer. In this process (part of) the gas mixture to be condensed coming from the stripper is introduced for example into a shell-and-tube heat exchanger.

The gas/liquid mixture formed in the high-pressure condenser section of the installation then flows through the tubes of the high-pressure condenser, where an exothermic carbamate reaction takes place. By designing this high-pressure condenser as a submerged condenser, residence time of the liquid carbamate in the high-pressure condenser is also ensured, so that urea formation partly takes place already here.

In the installation the carbamate stream coming from the high-pressure condenser flows together with the urea already formed and water to the first reactor section of the vertically placed combined reactor. In this reactor section part of the endothermic urea reaction takes place.

The urea solution from the first reactor section is discharged to the second reactor section. This takes place preferably by making use of gravity, for instance via a downcomer. This downcomer can be installed both inside and outside the combined reactor. The transfer of the urea solution from the first to the second reactor section can also be carried out with an ejector driven by the ammonia required for the process.

In the second reactor section the urea reaction is completed. If necessary for process operation purposes a small portion of the fresh carbon dioxide is fed to the second reactor section.

As an alternative to the fresh carbon dioxide that is added to the second reactor section, a portion of the stripping gases can also be used. Preferably, 5–50% of the stripping gas is passed to the second reactor section using an ammonia-driven ejector, and more in particular 10–30% of the stripping gas is passed to the second reactor section using an ammonia-driven ejector. The ammonia needed to drive the ejector can be used both in liquid form and in vapour form. The other stripping gas in the installation is preferably passed to the first reactor section of the vertically placed combined reactor via the high-pressure condenser section. Use can of course also be made of a combination of both fresh carbon dioxide and stripping gases from the stripper to allow the exothermic carbamate reaction in the second reactor section to proceed.

The reactor off-gases with still free ammonia and carbon dioxide are washed in the scrubber section of the installation with the low-pressure carbamate stream that is formed in the further recovery and/or the ammonia feed. Preferably, the fresh ammonia feed is used wholly or partially as an absorbent in the scrubber section of the installation. In this scrubber total as well as partial washing of this unconverted ammonia and carbon dioxide can take place. If necessary, the reactor off-gases can be freed of remaining ammonia and carbon dioxide outside the combined reactor.

The conversion of carbamate into urea and water in the installation can be accomplished by ensuring a sufficiently long residence time of the reaction mixture in the vertically placed combined reactor. The residence time will in general be more than 10 min., preferably more than 20 min. The residence time will in general be shorter than 2 hours, preferably shorter than 1 hour. At a higher temperature and pressure in the combined reactor a short residence time is usually sufficient to obtain a high conversion.

The installation according to the present invention can be applied in new plants (grassroots plants) as well as for the improvement and optimization (revamping) of existing urea plants of any design.

The invention therefore also relates to a method for improving and optimizing (revamping) of existing urea plants by installing an installation according to the present invention. In particular, the invention relates to a method for improving and optimizing existing urea plants by replacing the existing reactor and high-pressure condenser with an installation according to the invention. Such replacement can be done in conventional plants as well as in stripping plants of any design.

Since the installation comprises a vertically placed reactor, this combined reactor needs only a limited floor area, which offers the exceptional advantage that the combined reactor can be installed at ground level, while the urea solution is discharged by gravity to the high-pressure stripper. Especially in revamping projects the available floor area is often limited and therefore the vertically placed combined reactor is eminently suitable for this. The vertically placed combined reactor is also an attractive alternative to, for example, the poolreactor.

The added advantage of the installation according to the invention in revamping of conventional plants is the fact that the steam consumption is comparable with the steam consumption in stripping plants, i.e. about 925 kg steam per tonne of urea. For a conventional urea plant this is a remarkable improvement.

A great advantage of the installation comprising the combined reactor comprising two reactor sections that are separated by a high-pressure condenser section is that it can be introduced into a plant with substantially lower investment costs, because due to the integration of a heat exchanger/high-pressure condenser and scrubber into a combined reactor fewer equipment items and lines—that must be resistant to high pressure in a very corrosive environment—are necessary. A further advantage is the installation at ground level, resulting in a less high plant structure. Installation at ground level is also possible for the second embodiment of the installation, in which the combined reactor comprises two reactor sections and in which the high-pressure condenser section is placed outside the combined reactor. The installation at ground level offers further advantages in terms of investment and also promotes safety.

The invention also relates to a urea plant in which the high-pressure section substantially consists of an installation according to the invention, comprising two reactor sections in a vertically placed combined reactor, a high-pressure condenser section and a high-pressure stripper. In particular, the invention relates to a urea plant in which the high-pressure section substantially consists of an installation according to the invention, the vertically placed combined reactor comprising two reactor sections that are separated by a high-pressure condenser section and in which also a high-pressure stripper is installed. The invention also relates to a urea plant in which the high-pressure section substantially consists of an installation comprising a vertically placed combined reactor comprising two reactor sections, a high-pressure condenser installed outside the reactor and a high-pressure stripper. The stripper used in the high-pressure section of a urea plant is preferably a $CO_2$ stripper. In particular, the invention relates to urea plant in which the high-pressure section can be placed at ground level and in which the urea solution is gravity-fed to the stripper.

By way of example the invention is further elucidated below on the basis of the following figures and examples.

FIG. 1: A schematic representation of part of a urea stripping plant according to the Stamicarbon $CO_2$ stripping process.

FIG. 2: A schematic representation of part of a new urea stripping plant according to the principle of the invention, the installation comprising a vertically placed combined reactor comprising two reactor sections that are separated by a high-pressure condenser section.

FIG. 3: A schematic representation of part of a new urea stripping plant according to the principle of the invention, the installation comprising a vertically placed reactor comprising two reactor sections that are separated by a high-pressure condenser section, with an ammonia ejector.

FIG. 4A: A schematic representation of part of a urea stripping plant according to the principle of the invention, the installation comprising a vertically placed combined reactor comprising two reactor sections that are separated by a high-pressure condenser section, with a stripping gas ejector.

FIG. 4B: A schematic representation of a urea stripping plant according to the principle of the invention, the installation comprising a vertically placed combined reactor comprising two reactor sections and a high-pressure condenser section placed outside the combined reactor, with a stripping gas ejector.

FIG. 5A: A schematic representation of part of a combined reactor, comprising two reactor sections that are separated by a high-pressure condenser section.

FIG. 5B: A schematic representation of part of a combined reactor, comprising two reactor sections.

In FIG. 1, R represents a reactor in a Stamicarbon $CO_2$ stripping plant in which carbon dioxide and ammonia are converted into urea. The urea synthesis solution (USS) leaving the reactor is sent to a $CO_2$ stripper (S), in which the USS is converted into a gas stream (SG) and a liquid stream (SUSS) by stripping the USS with $CO_2$. The gas stream (SG) leaving the $CO_2$ stripper substantially consists of ammonia and carbon dioxide and the SUSS is the stripped USS. The stream containing the stripped urea synthesis solution (SUSS) is passed to the urea recovery (UR), where urea (U) is recovered and water (W) is discharged. In the UR a low-pressure ammonium carbamate stream (LPC) is obtained, which is fed to the high-pressure scrubber (SCR). In this scrubber the LPC is contacted with the gas stream coming from the reactor (RG), which substantially consists of ammonia and carbon dioxide but which also contains the inerts (non-condensable components) present in the carbon dioxide feed and the ammonia feed. Normally, heat is also carried off in the SCR. In this example, the enriched carbamate stream (EC) leaving the SCR is passed to the high-pressure condenser (C), in which the SG stream is condensed with the aid of EC. This condensation may also be effected without adding EC to C; in this case it is logical for EC to be added to the reactor R direct. The resulting high-pressure carbamate stream (HPC) is returned to the reactor. In this example, the fresh ammonia is recycled via the high-pressure carbamate condenser (C) but it may of course also be admitted elsewhere in the R→S→C→R loop or in the R→SCR→C→R loop.

In FIG. 2 ECR represents a combined reactor comprising two reactor sections that are separated by a high-pressure condenser section in a $CO_2$ stripping plant in which carbon dioxide and ammonia are converted into urea. The urea solution (UCS) coming from the first section of the reactor is supplied to the second section of the reactor in which the urea reaction is completed. The urea solution (USS) coming from the second section of the reactor is transferred to a $CO_2$ stripper (S), in which the USS is converted into a gas stream (SG) and a liquid stream (SUSS) by stripping the USS with carbon dioxide. The gas stream leaving the stripper (SG) substantially consists of ammonia and carbon dioxide and the SUSS is the stripped USS. The stream containing the stripped urea synthesis solution SUSS is transferred to the urea recovery (UR), where urea (UR) is recovered and water (W) is discharged. In the UR a low-pressure ammonium carbamate stream (LPC) is obtained, which is fed to a scrubber bed in the combined reactor. In this scrubber the LPC is contacted with the gas stream (CRG) coming from the first section of the combined reactor, which substantially consists of ammonia and carbon dioxide, but which in addition contains the inerts (non-condensable components) present in the carbon dioxide feed and the ammonia feed. Also, in this figure the ammonia feed is by way of example used as absorbent in this scrubber. The enriched carbamate stream (EC) coming from this scrubber is transferred to the high-pressure condenser section of the combined reactor. Via a downcomer, which may be situated outside the reactor but is preferably situated within the reactor, this carbamate stream (of high pressure) is contacted with the ammonia and carbon dioxide vapour in the high-pressure condenser section of the combined reactor, which is of the submerged type with limited residence time. The carbamate and the urea formed in this high-pressure condenser section are transferred to the first reaction section of the combined reactor, in which the urea reaction takes place to a substantial degree. The urea solution, which also contains unconverted carbamate (UCS), is gravitated to the second reaction section of the combined reactor. For stirring of the compartments in this reactor section and for completion of the urea reaction, fresh $CO_2$ is fed to this second reactor section. The gas stream (RG) leaving the second reactor section, which stream substantially consists of ammonia and carbon dioxide but in addition contains the inerts (non-condensable components) present in the carbon dioxide feed, is fed to the high-pressure condenser section of the combined reactor. The separation of the gas stream leaving the second reactor section from the urea synthesis solution (USS) leaving this reactor section preferably takes place in the combined reactor, but it can also take place in a gas/liquid separator installed for the purpose that is situated outside the combined reactor.

Figure 4A:
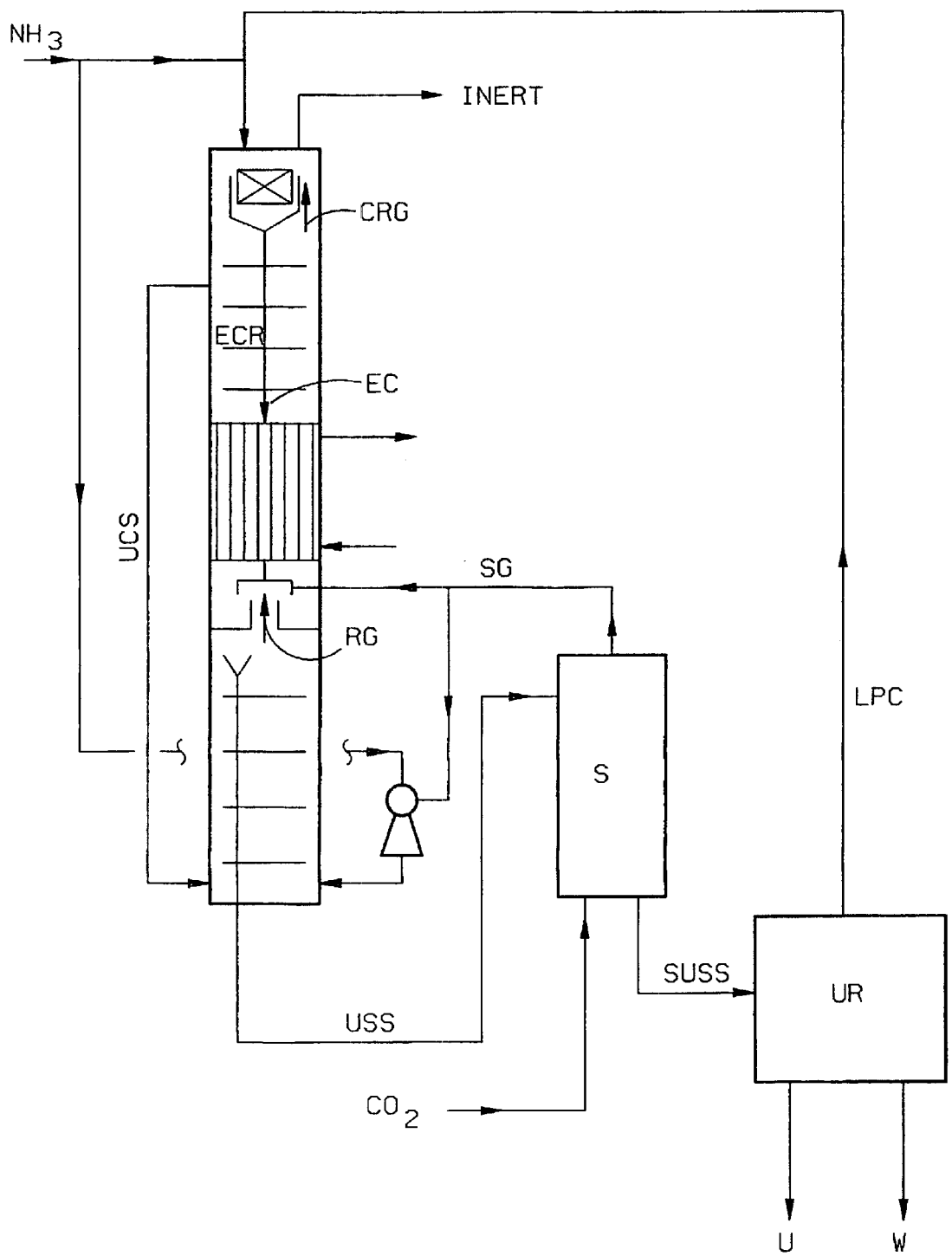
FIG. 4A is a diagrammatic representation of a urea stripping plant as in FIG. 2 in which an ejector driven by the required ammonia is used to transfer a portion of the stripped gas (SG) to the second reactor section for stirring of the compartments in this second reactor section and for completion of the urea reaction.
Figure 4B:
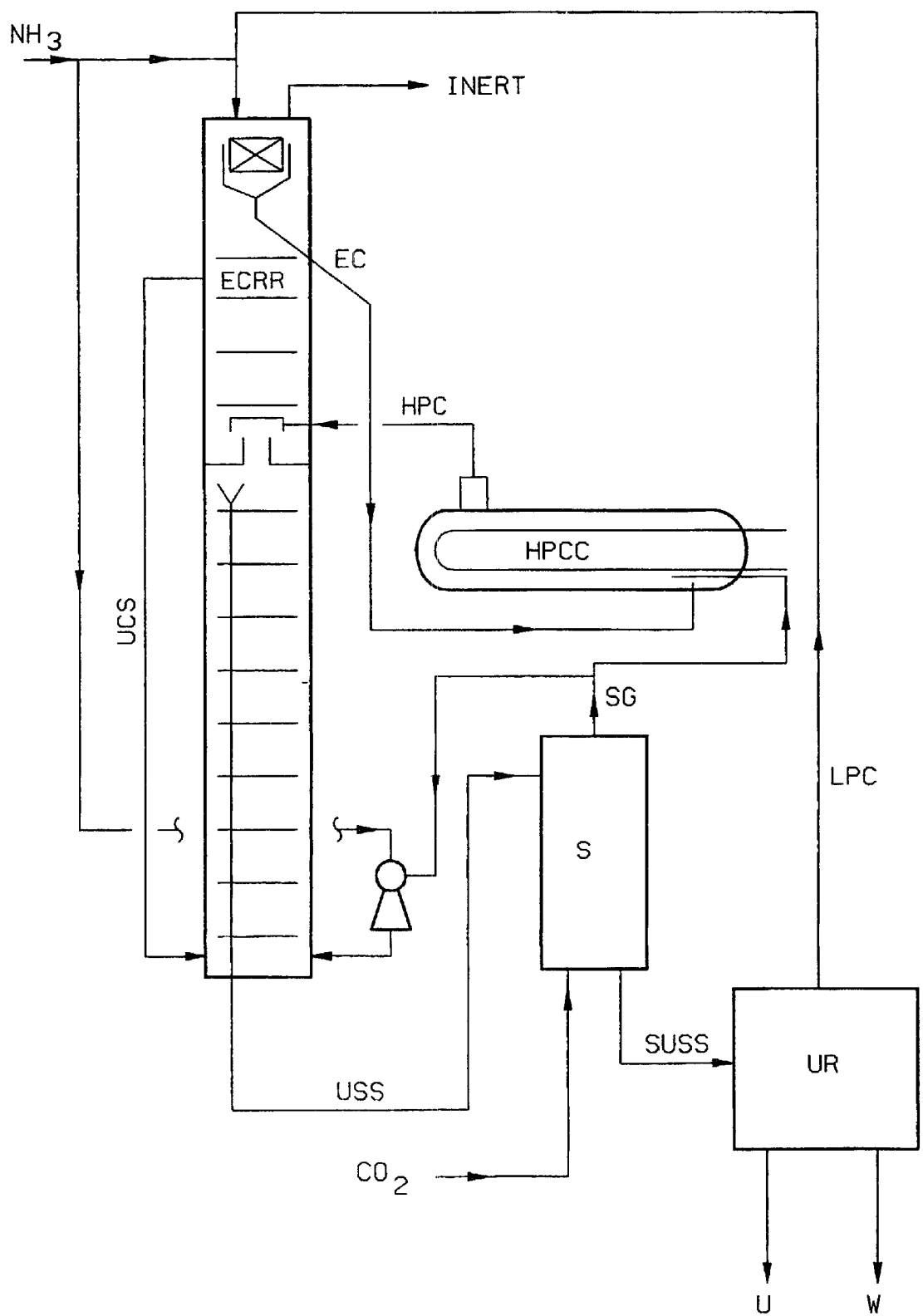

FIG. 4B is a diagrammatic representation of a urea plant as in FIG. 4A in which the vertical placed combined reactor comprising two reactor sections that are separated by a high-pressure condenser section has been replaced by a vertically placed combined reactor comprising two reactor sections (ECRR) and a high-pressure condenser section placed outside the combined reactor (HPCC). The high-pressure condenser section placed outside the combined reactor is, according to a preferred embodiment of the invention, shown as a submerged high-pressure condenser.

Figure 2:
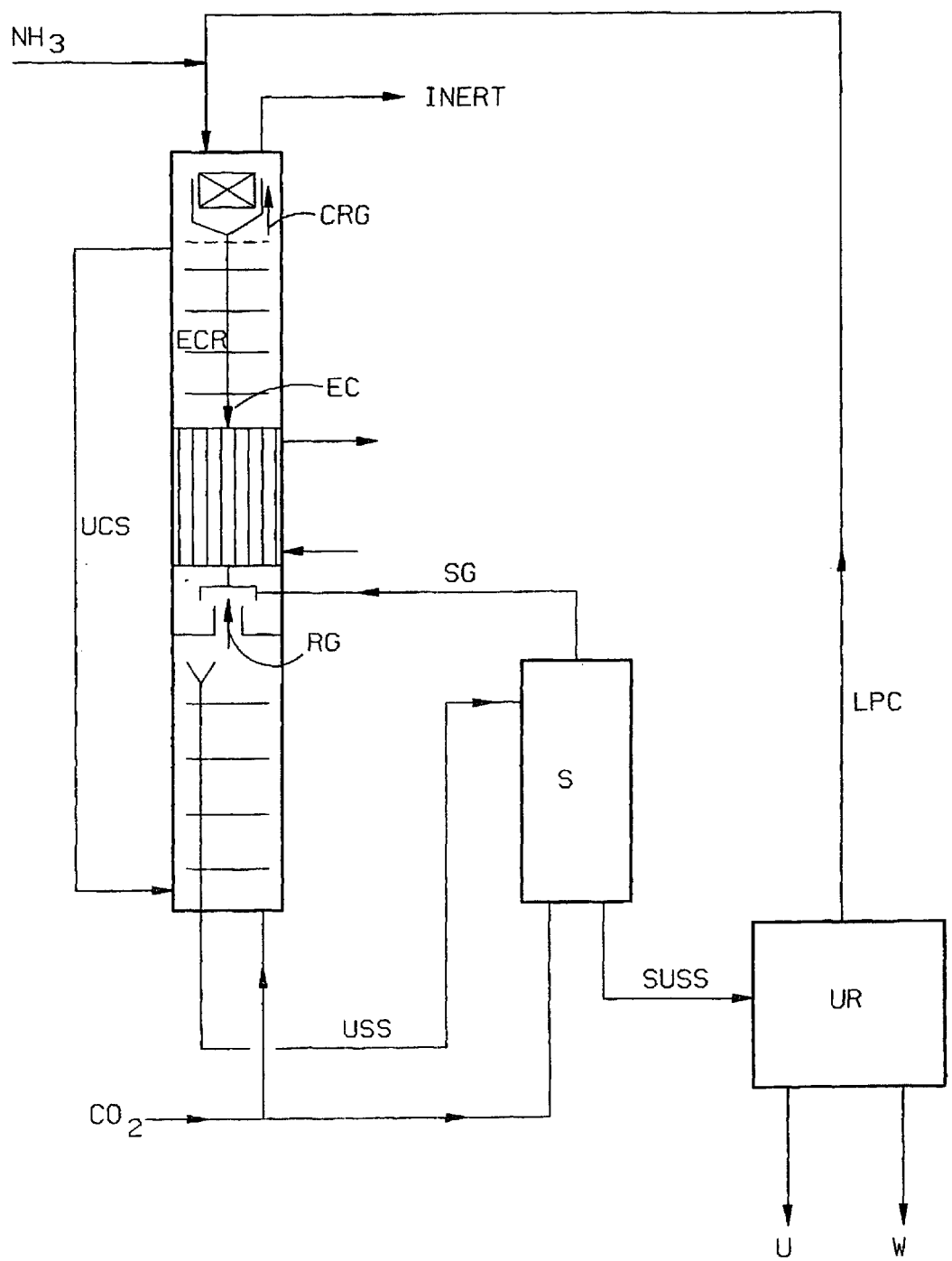
Figure 3:
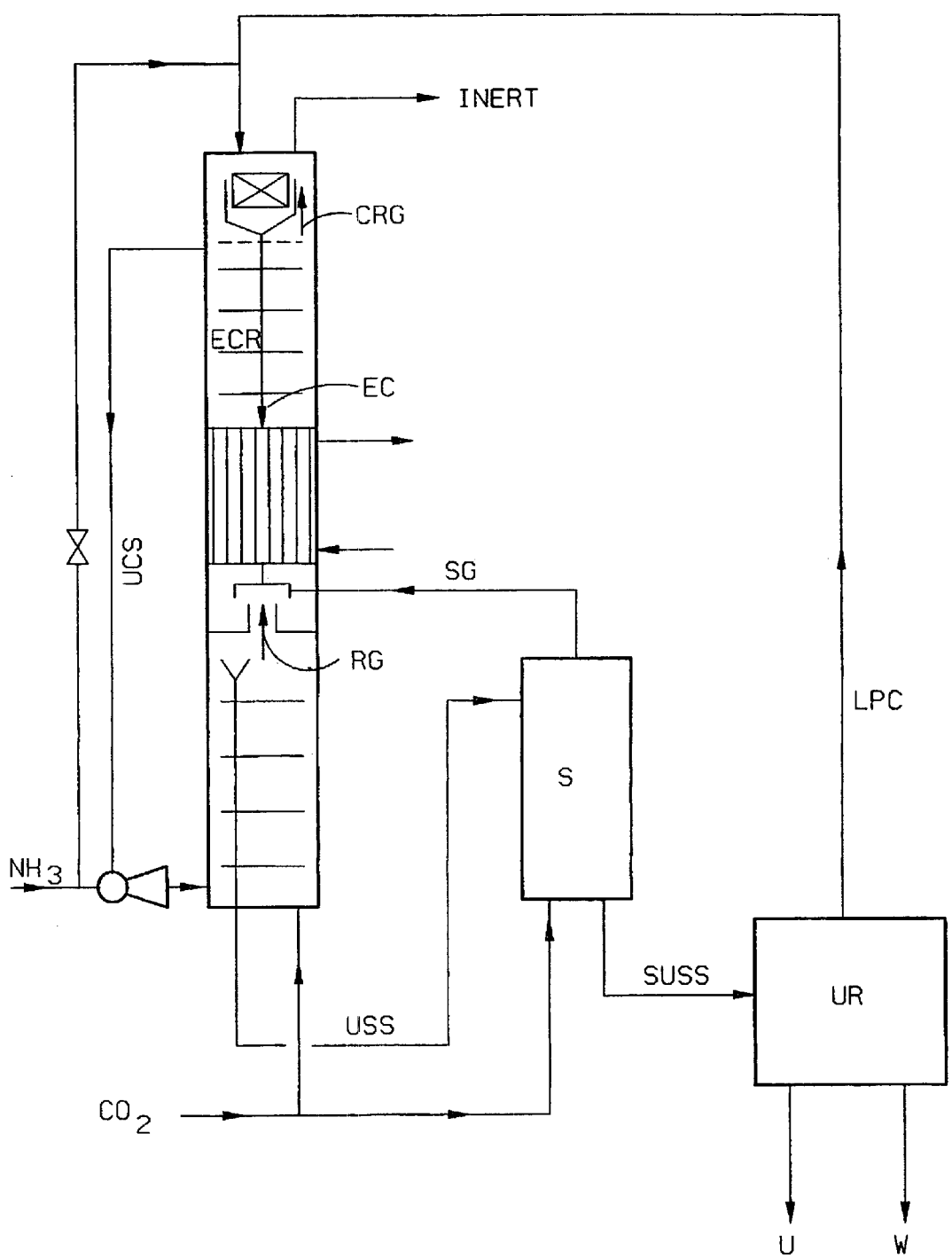
FIG. 3 is a diagrammatic representation of part of a urea plant as in FIG. 2 in which the urea solution (UCS), which also contains unconverted carbamate, is transferred to the second reaction section of the combined reactor according to the first embodiment by means of an ammonia-driven ejector.
Figure 5A:
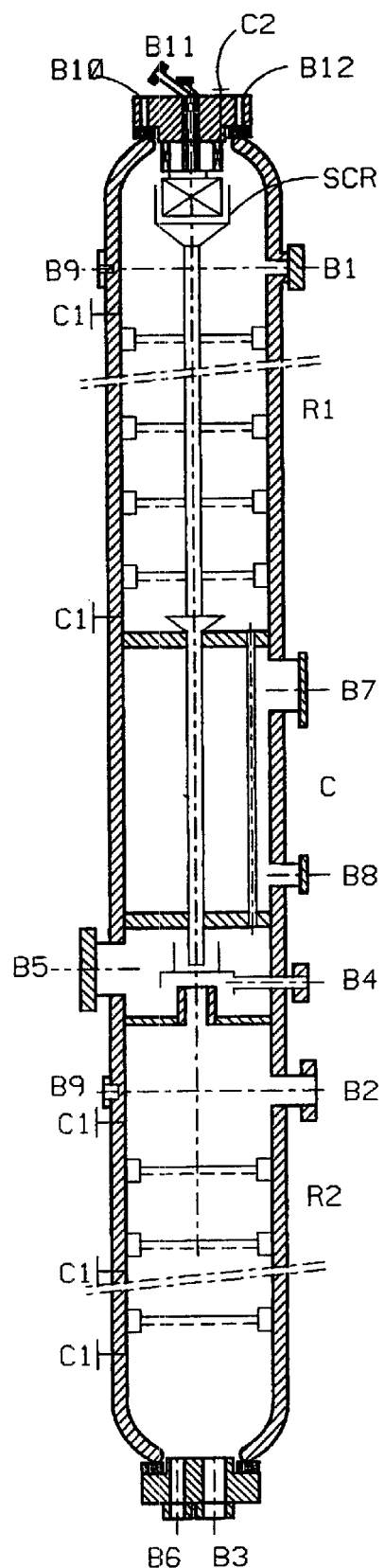
Figure 5B:
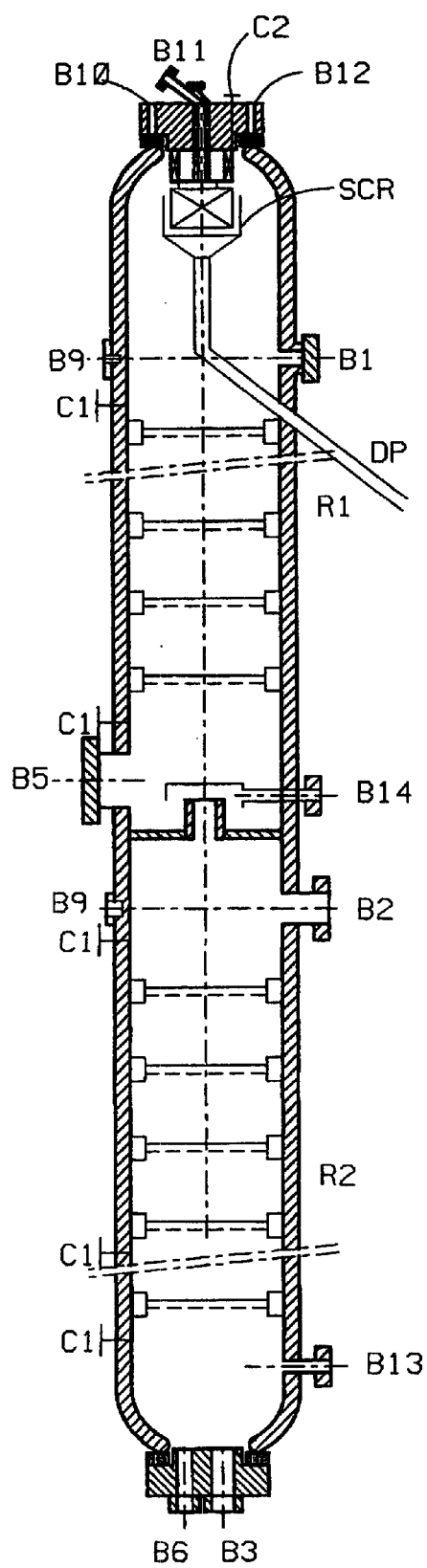

FIG. 5A is a diagrammatic representation of part of the vertically placed combined reactor, comprising two reactor sections that are separated by a high-pressure condenser section, that is used in FIGS. 2,3 and 4A. In this figure the symbols denote the following:

R1 first reactor section
R2 second reactor section
C high-pressure condenser section
SCR scrubber section
B1 overflow of the first reactor section
B2 overflow of the second reactor section B3 urea synthesis solution feed to second reactor section
B4 stripper gas feed to high-pressure condenser section
B5 manhole
B6 $CO_2$ feed to second reactor section
B7 steam/condensate discharge of high-pressure condenser section
B8 condensate feed to high-pressure condenser section
B9 radioactive level measurement
B10 low-pressure carbamate/ammonia feed
B11 reactor off-gas discharge
B12 blow-off/safety valve
C1 thermocouples
C2 thermocouples FIG. 5B is a diagrammatic representation of the vertically placed combined reactor used in FIG. 4B. The codes used are the same as in FIG. 5A. Further, in FIG. 5B:
DP is a downcomer through which the enriched carbamate stream leaving the scrubber is transferred to the high-pressure condenser
B13 is the stripper gas feed to the second reactor section
B14 is the high-pressure carbamate feed from the condenser.

The invention is elucidated further by means of the following examples.

Comparative Example A

Figure 1:
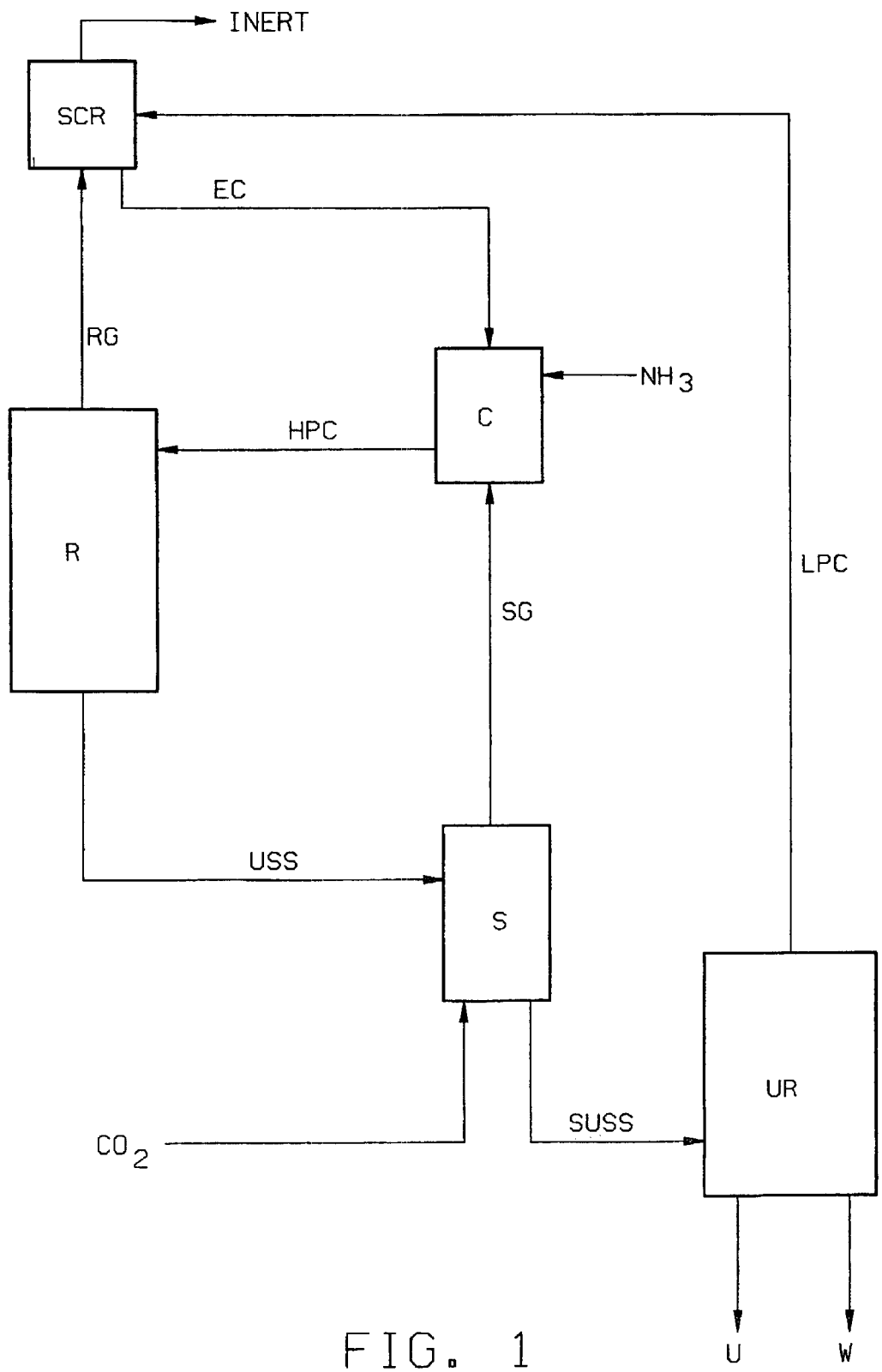

Table 1 below presents the compositions in percent by weight of the various streams for a Stamicarbon $CO_2$ stripping plant as shown in FIG. 1. From the compositions it follows that the urea conversion has taken place almost entirely in the reactor (R) and the carbamate condensation has taken place in the high-pressure condenser (C).

TABLE 1

| Stream | Urea | $NH_3$ | $CO_2$ | $H_2O$ | Inerts |
|---|---|---|---|---|---|
| USS | 33.0 | 30.5 | 18.0 | 18.5 | — |
| $CO_2$ | — | — | 96.0 | 0.5 | 3.5 |
| SUSS | 55.0 | 7.8 | 10.5 | 26.7 | — |
| SG | — | 41.0 | 54.5 | 3.5 | 1.0 |
| $NH_3$ | — | 99.6 | — | 0.4 | — |
| HPC | — | 49.5 | 42.0 | 8.0 | 0.5 |
| RG | — | 50.0 | 39.5 | 3.5 | 7.0 |
| EC | — | 39.0 | 39.0 | 22.0 | — |
| LPC | — | 30.0 | 37.0 | 33.0 | — |
| Inerts | — | 5.5 | 5.0 | 0.5 | 89.0 |

Example 1

Table 2 below presents the compositions in percent by weight of the various streams for a Stamicarbon $CO_2$ stripping plant as shown in FIG. 2, in which a combined reactor comprising two reactor sections that are separated by a high-pressure section is installed. A substantial part of the urea reaction takes place in the first section of the combined reactor and the urea reaction is completed in the second reactor section of the combined reactor.

TABLE 2

| Stream | Urea | $NH_3$ | $CO_2$ | $H_2O$ | Inerts |
|---|---|---|---|---|---|
| USS | 35.5 | 29.5 | 16.5 | 18.5 | — |
| $CO_2$ | — | — | 96.0 | 0.5 | 3.5 |
| SUSS | 55.0 | 7.8 | 10.5 | 26.7 | — |
| SG | — | 40.0 | 54.0 | 3.5 | 2.5 |
| $NH_3$ | — | 99.6 | — | 0.4 | — |
| UCS | 23.5 | 34.5 | 26.0 | 16.0 | — |

TABLE 2-continued

| Stream | Urea | $NH_3$ | $CO_2$ | $H_2O$ | Inerts |
|---|---|---|---|---|---|
| CRG | — | 56.0 | 37.0 | 2.5 | 4.5 |
| RG | — | 39.0 | 39.0 | 22.0 | — |
| LPC | — | 30.0 | 37.0 | 33.0 | — |
| Inerts | — | 5.5 | 5.0 | 0.5 | 89.0 |

What is claimed is:
1. Installation for the preparation of urea from ammonia and carbon dioxide, characterized in that the installation comprises two reactor sections in a vertically placed combined reactor and a high-pressure condenser section.
2. Installation according to claim 1, characterized in that the installation comprises a vertically placed combined reactor comprising two reactor sections that are separated by a high-pressure condenser section.
3. Installation according to claim 1, characterized in that the installation comprises a vertically placed combined reactor comprising two reactor sections and a high-pressure condenser section placed outside the combined reactor.
4. Installation according to claim 2, characterized in that in the combined reactor the high-pressure condenser section is located below the reactor section in which the scrubber is placed and above the second reactor section.
5. Installation according to claim 3, characterized in that in the combined reactor the reactor section in which the scrubber is located is placed above the second reactor section.
6. Installation according to claim 3, characterized in that the high-pressure condenser section placed outside the reactor is located below the scrubber of the upper reactor section of the combined reactor.
7. An installation according to claim 1, wherein the reactor sections in the combined reactor are provided with means that ensure that the synthesis solution substantially flows through the reactor as a plug flow.
8. An installation according to claim 1, wherein the number of compartments in the reactor sections of the combined reactor, in the form of series-arranged CSTRs, is greater than 2.
9. An installation according to claim 3, wherein the high-pressure condenser section is designed as a horizontally placed submerged condenser.
10. An installation according to claim 1, wherein the high-pressure condenser section is designed as a submerged high-pressure condenser.
11. A process for the preparation of urea from ammonia and carbon dibxide, wherein the preparation takes place wholly or partly in an installation according to claim 1.
12. A process for the preparation of urea from ammonia and carbon dioxide, wherein the gas stream leaving the stripper is fed wholly or partly to the high-pressure condenser section of an installation according to claim 1.
13. A process according to claim 11, wherein the gas stream leaving the stripper is wholly or partly condensed in the carbamate stream that is transferred from the scrubber to the high-pressure condenser section through a downcomer.
14. Process according to claim 11, characterized in that a portion of the gas stream leaving the stripper is fed to the second reactor section in the vertically placed combined reactor via an ammonia-driven ejector.
15. Process according to claim 14, characterized in that 5–50% of the gas stream leaving the stripper is fed to the second reactor section in the vertically placed combined reactor via an ammonia-driven ejector.

16. Process according to claim 15, characterized in that 10–30% of the gas stream leaving the stripper is fed to the second reactor section in the vertically placed combined reactor via an ammonia-driven ejector.

17. A process according to claim 14, wherein the remainder of the gas stream from the stripper is passed via the high-pressure condenser to the first reactor section, where the scrubber is located.

18. A process according to claim 11, wherein the ammonia feed is wholly or partially used as absorbent in the scrubber section of the combined urea reactor.

19. A method for improving and optimizing an existing urea plant, wherein an installation according to claim 1 is installed.

20. A method for improving and optimizing an existing urea plant, wherein the existing reactor and high-pressure condenser are replaced by an installation according to claim 1.

21. A urea plant, wherein the high-pressure section substantially consists of an installation according to claim 1 and a high-pressure stripper.

* * * * *